United States Patent [19]

Ellin et al.

[11] Patent Number: 4,590,166

[45] Date of Patent: May 20, 1986

[54] METHOD FOR SEPARATING AND MEASURING THE AMOUNT OF POLAR COMPOUNDS AND THEIR METABOLITES IN AQUEOUS SOLUTIONS

[75] Inventors: Robert I. Ellin, Baltimore; Peter Zvirblis, Edgewood, both of Md.

[73] Assignee: The United States of America as represented by the Secretary of the Army, Washington, D.C.

[21] Appl. No.: 477,479

[22] Filed: Mar. 11, 1983

[51] Int. Cl.$^4$ .................. G01N 1/18; G01N 30/06; G01N 33/48

[52] U.S. Cl. .................. 436/96; 436/111; 436/128; 436/131; 436/161; 436/178

[58] Field of Search .............. 436/96, 106, 111, 161, 436/177, 178, 128, 131; 210/656, 659; 73/61.1 C

[56] References Cited

FOREIGN PATENT DOCUMENTS 0026747 2/1982 Japan .................. 436/161

OTHER PUBLICATIONS

Davison et al, Meth. and Find. Exptl. Clin. Pharmacol., vol. 2, No. 2, pp. 77–82 (1980).

Yakatan et al, J. of Chromatography, vol. 164, pp. 399–403 (1979).

De Ruyter et al, J. of Chromatagraphy, vol. 183, pp. 193–201 (1980).

Jsuda et al, J. of Chromat., 158 (1978) pp. 227–232.

De Ruyter et al, Chemical Abstracts, vol. 93, No. 93:142550y (1980).

Chan et al, Chemcial Abstracts, vol. 90, No. 90:132478e (1979).

Coper et al, Chemical Abstracts, vol. 81, No. 101497v (1974).

Yakatan et al, Chemical Abstracts, vol. 92, No. 92:121426b (1980).

*Primary Examiner*—David L. Lacey
*Assistant Examiner*—Robert J. Hill, Jr.
*Attorney, Agent, or Firm*—John H. Raubitschek; John M. Petrunico; Werten F. W. Bellamy

[57] ABSTRACT

This invention relates to a novel method for separating and measuring the amount of polar compounds, such as pyridostigmine, acetylcholine, neostigmine, and edrophonium, and their metabolites in aqueous solutions. The method is used to determine the urinary excretion and plasma levels of polar compounds administered to animals.

21 Claims, 5 Drawing Figures

METHOD FOR SEPARATING AND MEASURING THE AMOUNT OF POLAR COMPOUNDS AND THEIR METABOLITES IN AQUEOUS SOLUTIONS

BACKGROUND OF THE INVENTION

Polar compounds such as pyridostigmine are used extensively in the treatment of patients with myasthenia gravis. Recently, pyridostigmine, in combined therapy with atropine and an oxime, was suggested as an antidote in organo phosphate poisonings as reported in *Toxicol. Appl. Pharmacol.*, Vol. 43 (1978), page 207. In cases where patients received oral doses of pyridostigmine, considerable inter-subject variation of blood levels was reported in *Neurology*, Vol. 26, (1976) at page 536. Maximum plasma levels after similar oral doses administered to man range from 1 to 200 mg/ml. The quantitative isolation and accurate determination of the drug in biological fluids would result in establishing pharmacokinetic constants for pyridostigmine administered alone and in combination with other drugs.

Pyridostigmine is generally separated from plasma by extraction of an ion-pair complex with organic solvent. Quantitation has been reported by spectrophotometric in *Z. Klin. Chem. Klin. Bio. Chem.*, Vol. 12 (1974), page 273, gas or liquid chromatographic analysis in *Methods Find. Exp. Clin. Pharmacol.*, Vol. 2 (1980), page 77. Spectrophotometric methods are not sensitive enough to measure pyridostigmine in plasma after administration to man of 30 to 60 mg doses. Pohlmann and Cohan's method reported in J. Chromatogr., Vol. 131 (1977), page 297, based on electron-capture gas chromatography, measures picogram amounts, but lacks selectivity. In *J. Chromatogr.*, Vol. 120 (1976), page 349, Chan et al. reported using an on-column gas chromatographic dequaternization method for selective and sensitive detection of nanogram amounts of pyridostigmine in plasma. Recently, two liquid chromatographic (LC) procedures have been introduced for determining pyridostigmine in *J. Chromatogr.*, Vol. 164 (1979), page 399 and *J. Chromatogr,*, Vol. 183 (1980), page 193.

DETAILED DESCRIPTION OF THE INVENTION

Figure 1:
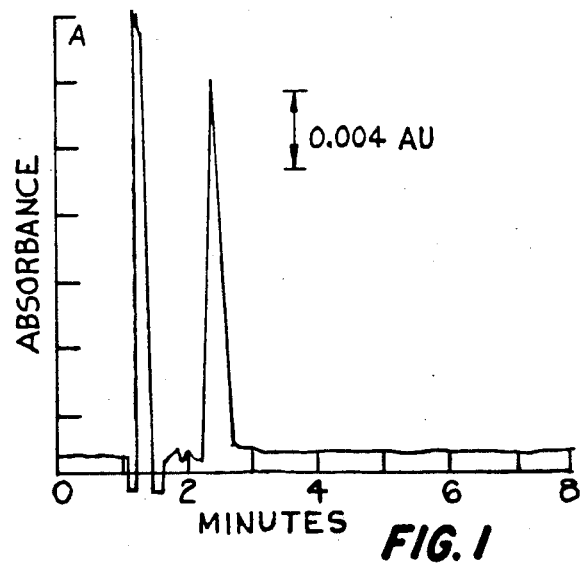
FIG. 1 is a liquid chromatogram of urine blank passed through Sep-Pak.

This invention relates to a novel and unique method which provides rapid, selective and quantitative recoveries of polar compounds such as pyridostigmine, acetylcholine, neostigmine, and edrophonium from aqueous solutions such as urine and plasma.

More precisely, this method provides for the separation of polar compounds and their metabolites from an aqueous solution comprising the steps of:

1. washing a cartridge which consists of a packing material of silanized silica gel coated with octadecyl silane with an alkanol containing 1 to 7 carbon atoms, preferably methanol followed by the washing of said cartridge with water;
2. preparing an alkaline solution of said aqueous solution by adding a sufficient amount of a basic substance such as an alkali metal hydroxide or carbonate, preferably sodium hydroxide or sodium carbonate to adjust the pH level within the range of 10 to 11, preferably 10.02 to 10.6, and most preferably 10.2–10.6;
3. separating any precipitate formed in step 2. from the remaining liquid phase by centrifugation;
4. passing the liquid phase separated in step 3. through the alkanol and water washed cartridge of step 1. which results in the binding of the compounds and their metabolites to the packing material within the cartridge; and
5. separating the compounds and their metabolites bound to the cartridge of step 4. by washing the cartridge with successive washings of water, an alkanol, and alkanol dilute acid-alkanol mixtures wherein the alkanol component contains 1 to 7, preferably 1 to 3 carbon atoms and the acid component is acetic or hydrochloric acid, and collecting the resultant liquid product.

In order to make a quantitative determination of the amount of a polar compound such as pyridostigmine, for example, and its metabolites present in an animal body fluid such as urine or plasma, the liquid product obtained in step 5. above is subjected to the following steps of treatment:

6. the liquid product obtained in step 5. is divided into fractions;
7. each of the fractions step 6. is then dried over nitrogen in a water bath, set at between 35° C. and 45° C., preferably 40° C.;
8. aqueous methanol, preferably a 45 to 55% methanol solution, is added to each dried fraction of step 7.;
9. a volume of the methanolic fraction prepared in step 8. equivalent to 1 ml of the aqueous solution (water, urine or plasma) is injected into a liquid chromatograph for quantitative analysis.

In the method of this invention, the liquid phase of step 3. is filtered through a filter, such as a Millex filter, when the animal body fluid is urine.

In step 1 of the method described above, the type of cartridge which consists of a silanized silica gel coated with octadecyl silane includes the use of the Sep-Pak TM cartridge.

EXPERIMENTAL PROCEDURES

Apparatus and reagents

Analyses were carried out using a Waters Accos. (Milford, MA, U.S.A.) Model 244 liquid chromatograph equipped with two Model 6000A high-pressure pumps, a U6K loop injector, a Model 450 variable-wavelength detector, a Model 440 dual-wavelength absorbance detector, a Houston Instruments Omni-Scribe A 5-000 dual-pen recorder, and a Shimadzu data processor. Hamilton syringes, 1-100 1, were used to inject samples into the chromatograph. A bench-top centrifuge (Clay-Adams) was used to spin down precipitates.

Solvents

Spectroquality solvents were used: methanol, acetonitrile, chloroform, carbon tetrachloride from Waters Assoc., heptane, hexane from Burdick & Jackson Labs., Muskegon, MI, U.S.A., amyl alcohol and cyclohexane from Fisher, Fairlawn, NJ, U.S.A. Distilled, deionized, and charcoal-filtered water was used for all solutions.

Chemicals

Pyridostigmine bromide, neostigmine bromide, and methyl-p-aminobenzoic acid (methylparaben) were obtained from U.S. Pharmacopeia Convention (Rockville, MD, U.S.A.); acetylcholine was from Sigma (St. Louis, MO, U.S.A.); 3-hydroxy-N-methyl pyridinium bromide, RO-1-5237, dimethylcarbamyl ester of 3-hydroxypyridine, RO-1-5142, and edrophonium hydrochloride, RO-2-3198 were from Hoffmann-La Roche (Nutley, NJ, U.S.A.); Pic B-8 reagent containing 1-octanesulfonic acid buffers was from Waters Assoc.; sodium carbonate, potassium carbonate, and sodium phosphate. All reagents were analytical grade or better.

Columns and packing material

A prepacked 300×4 mm I.D. Bondapak $C_{18}$ column, particle size 10 μm, Sep-Pak TM cartridge, $C_{18}$ on porous silica, particle size 50 μm; Corasil Type II, particle size 31–50 μm were all obtained from Waters Assoc. Millex 0.45 μm filter units were from Millipore (Bedford, MA, U.S.A.) and B-D Yale syringes from Becton Dickinson (Rutherford, NJ, U.S.A.).

EXAMPLES

The working examples set forth below illustrate, without any implied limitation, the method as applied to the separation of a representative compound i.e. pyridostiqmine, from aqueous solutions such as water, urine and plasma.

EXAMPLE 1

A sample of pyridostigmine bromide was dried in vacuum according to specification in USP XIX. A dilute standard containing 1 mg/ml of pyridostigmine bromide was prepared in $10^{-3}N$ hydrochloric acid and stored in a refrigerator at 4° C. Subsequent dilutions were prepared from this standard. A Sep-Pak cartridge was washed with 5 ml of methanol followed by 5 ml of water. Flow-rates were manually controlled to 5–10 ml/min of solvent.

Volumes of urine (1–10 ml) were brought to pH 10.2–10.6 with sodium hydroxide. Resulting precipitates were centrifuged for 1 min in a bench-top centrifuge. Supernatants were placed in a glass syringe and passed through a Millex filter. The syringe and filter unit were attached to the Sep-Pak cartridge and the urine passed through the Sep-Pak cartridge. The cartridge was washed with 5 ml of water, then 5 ml of methanol. About 3 ml of air were introduced into the Sep-Pak to eliminate excess methanol. A glass syringe containing 2 ml of 0.1N acetic acid in methanol was attached to the Sep-Pak. One or two 1-ml fractions were collected in separate test tubes and 25 μl of internal standard solution added. Each tube was taken to dryness over nitrogen in a water bath set at 40° C. and reconstituted with microliter volumes of 50% methanol. A volume equivalent to 1 ml of urine could be injected into the liquid chromatograph for quantitative analysis.

EXAMPLE 2

The procedure of Example 1 was followed for separating and determining the amount of pyridostigmine present in plasma except that the Millex filtration procedure was unnecessary.

Liquid chromatography

For LC analysis, a 300×3.9 mm I.D. Bondapak column prepacked with octadecylsilane bonded to 10 μm silica was used in the chromatography of all samples. The mobile phase consisted of 0.005M 1-octanesulfonic acid (Pic B-8) in water and acetonitrile (prepared by mixing the contents of a prepackaged reagent bottle with 800 ml of water, 200 ml of acetonitrile, and 5 ml of acetic acid). The solvent was pumped through the column at a flow-rate of 2.5 ml/min. Column pressures were generally around 13.8 MPa. All separations were performed at ambient temperatures. Samples were introduced into the column through a continuous flow loop injector. The volumes of sample injected were between 5 and 100 μl. Absorbances were measured in the variable-wavelength detector at 270 nm. As reference standards individual solutions containing 0.05, 0.12, 0.25, 1.0, 2.5, or 5.0 μg of pyridostigmine per ml of water were prepared. Similarly, concentrations of pyridostigmine bromide were prepared by adding aqueous concentrates to human urine or plasma. Internal standard solutions contained p-hydroxybenzoic acid methyl ester (methylparaben), 2.5–5.0 mg in 100 ml of water. Peak areas were measured and concentrations determined by an on-line computing integrator.

TEST METHODS

Animal studies

For animal studies, rats weighing 175–225 g were placed in metabolic cages and deprived of solid food for 14 hours. For urine studies they were hydrated by the administration of 2.5 ml per 100 g of warm water by stomach tube. This was repeated after 1 hour. An 80 μg aliquot of pyridostigmine in 0.2 ml water was injected intramuscularly into a hind limb. Urine free from feces was collected over a period of 24 hours. In blood studies a similar dose was administered intramuscularly. At selected intervals over a period of 1 hour blood specimens were collected from excised hearts.

Test Results

Figure 2:
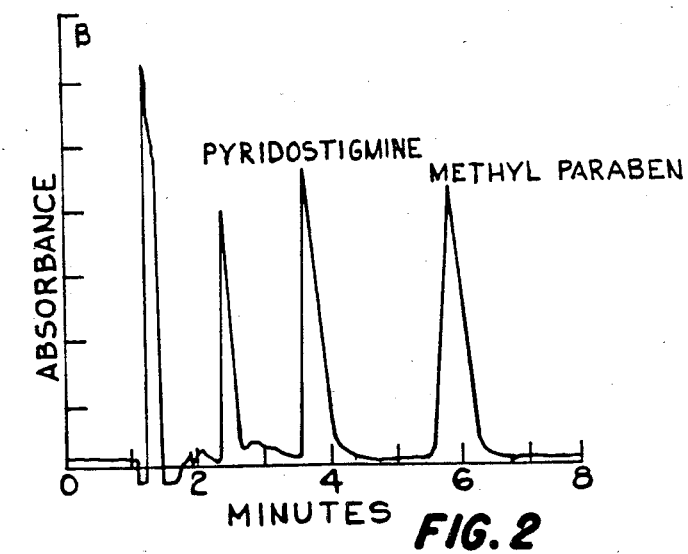
FIG. 2 is a liquid chromatogram of pyridostigmine isolated from urine by a Sep-Pak cartridge wherein methylparaben is the internal standard.

A typical liquid chromatogram of pyridostigmine recovered from the drug added to human urine is shown in FIGS. 1 and 2. In FIG. 1, liquid chromatograms of (A) urine blank passed through Sep-Pak whereas in FIG. 2, (B) pyridostigamine was isolated from urine by a Sep-Pak cartridge. Methylparaben is the internal standard.

Figure 3:
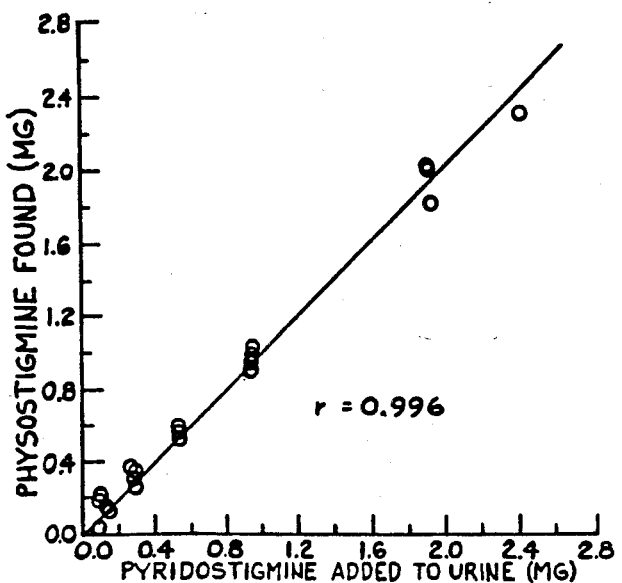
FIG. 3 represents the standard curve for recoveries of concentrations of pyridostigmine bromide in urine.

Retention time for pyridostigamine is 3.68 min, for methylparaben 5.93 min. Concentration levels ranging from 49 to 4900 ng/ml were assayed. Urine samples (5 ml) were generally used and volumes equivalent to 1 ml could be injected in the liquid chromatograph for analysis. Only when volumes greater than 5 ml were used were small interferences from urine noted. Two separate concentrations of internal standard were used: 2.5 μg/ml for concentrations of pyridostigmine up to 250 μg/ml, and 5 μg/ml for concentrations greater than 250

μg/ml. A linear regression analysis of the data is shown in FIG. 3. The following values were obtained: r (coefficient of correlation) is 0.996; slope is 0.9914; y-intercept at 0.0432; standard error of the slope, 0.0207. FIG. 3 depicts the standard curve for recoveries of concentrations of pyridostigmine bromide in urine. To demonstrate the suitability of this procedure and method for pyridostigmine in blood, pooled plasma was obtained from normal blood samples. Pyridostigmine was added to human plasma in concentrations of 40 ng/ml to 20 μg/ml. Rocoveries from 5-ml plasma samples are shown in Table I. Recoveries were 90–95% and 95–100% in the 40–100 and 100–5000 ng/ml levels, respectively. Chromatograms of pyridostigmine isolated from plasma had no interfering endogenous peaks. A correlation coefficient of 0.999 was obtained from linear regression data, with a slope of 0.9754 and the y-intercept at 0.0700. The standard error of the slope was 0.00739. Similar results occurred with pyridostigmine added to rat urine and plasma.

TABLE I

RECOVERY OF PYRIDOSTIGMINE BROMIDE ADDED TO 5 ml HUMAN PLASMA SAMPLES

| Sample No. | Pyridostigmine added (ng/ml) | Pyridostigmine found* (ng/ml) |
|---|---|---|
| 1 | 39 | 35 |
| 2 | 78 | 71 |
| 3 | 100 | 107 |
| 4 | 156 | 153 |
| 5 | 313 | 305 |
| 6 | 400 | 390 |
| 7 | 625 | 625 |
| 8 | 1250 | 1312 |
| 9 | 4000 | 4330 |

*Average of 3 determinations.

Separation of metabolites of pyridostigmine

Figure 4:
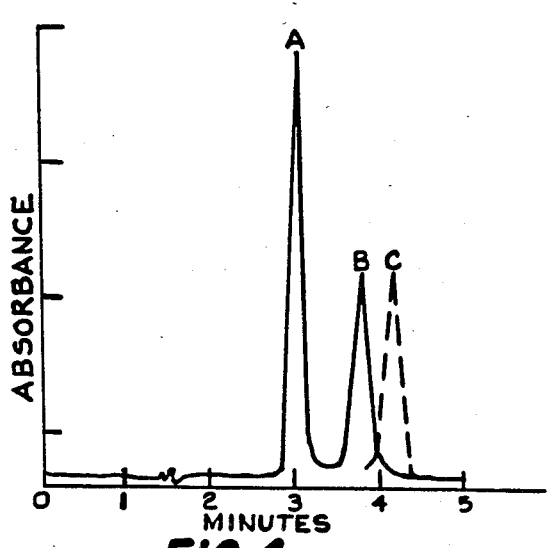
FIG. 4 is a liquid chromatogram of pyridostigmine and metabolites having the peaks designated as (A) (3-hydroxy-N-methyl pyridinium bromide (RO-1-5237), (B) dimethylcarbamyl ester of 3-hydroxypyridine (RO-1-5142), and (C) pyridostigmine bromide wherein low concentrations of the components B and C are resolved.
Figure 5:
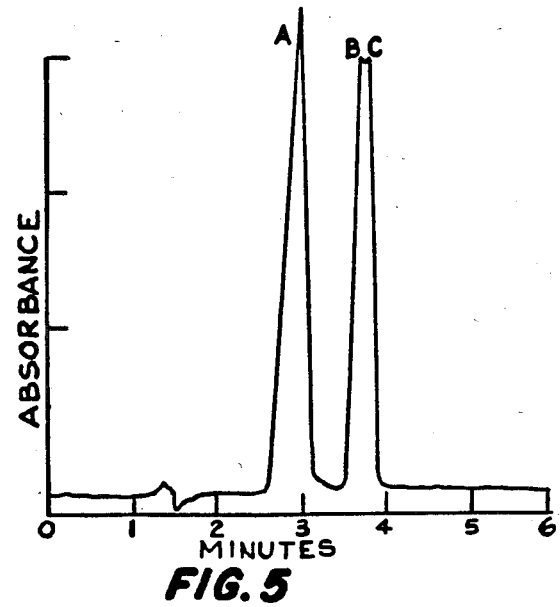
FIG. 5 is a liquid chromatogram of pyridostigmine and metabolites having peaks designated as (A), (B) and (C), as defined herein above wherein the components B and C are unresolved at high concentration levels when assayed only by liquid chromatographic procedures.

Chromatograms of pyridostigmine and two reported metabolites, RO-1-5237 and RO-1-5142, in aqueous solution are shown in FIGS. 4 and 5. As seen in FIGS. 4 and 5, solutions containing pyridostimine and RO-1-5142 could produce overlapping peaks and would not be quantitated by LC analysis. However, were these two products present together in a biological sample, they would be separated quantitatively by the Sep-Pak isolation procedure. The pyridostigmine would be retained on the cartridge, while the RO-1-5142 is eluted in the methanol wash. Were the RO-1-5237 metabolite and pyridostigmine present together in a sample, the former would be eluted in the water wash, the pyridostigmine would be retained. Additionally, the two could be separated and quantitated during the LC analysis.

FIGS. 4 and 5 depict liquid chromatograms of pyridostigmine and metabolites. Peaks: (A) 3-hydroxy-N-methyl pyridinium bromide (RO-1-5237), (B) dimethylcarbamyl ester of 3-hydroxypyridine (RO-1-5142), and (C) pyridostigmine bromide. In FIG. 4, low concentrations of components B and C are resolved. However, in FIG. 5, components B and C are unresolved at high concentration levels when assayed only by LC.

Influence of inorganic ions on the binding and isolation of pyridostigmine from a Sep-Pak cartridge Solutions of 0.1M sodium chloride, 0.1M sodium bromide, and 0.02M phosphate buffer were spiked with pyridostigmine bromide to make final concentrations of 20 μg/ml. A 3-ml aliquot of each solution was assayed separately by the procedure described in this paper. Results are presented in Table II. The isolation and quantitation of pyridostigmine in aqueous solutions of sodium hydroxide and sodium carbonate at pH 10–10.5 have been shown to be quantitative and nearly quantitative. Lower recoveries were obtained from sodium chloride and sodium bromide.

TABLE II

RECOVERIES (%) OF PYRIDOSTIGMINE FROM AQUEOUS SOLUTIONS OF SODIUM CHLORIDE, SODIUM BROMIDE, AND PHOSPHATE BUFFER AFTER SEPARATION BY SEP-PAK AND ANALYSIS BY LIQUID CHROMATOGRAPHY

|  | Sodium chloride solution | Sodium bromide solution | Phosphate buffer |
|---|---|---|---|
| Amount pyridostigmine bromide added (μg) | 59.2 | 58.8 | 58.2 |
| Sample eluate (3 ml) | 1.6 | 0 | 0 |
| Water wash (5 ml) | 1.7 | 0 | 0 |
| Alcohol wash (5 ml) | 30.9 | 25.9 | 0 |
| Acetate-methanol (1 ml) | 23.4 | 18.7 | 57.1 |
| Acetate-methanol (1 ml) | 4.0 | 3.7 | 2.2 |
| % Recovery, total | 103.1 | 82.1 | 101.9 |
| acetate-methanol | 46.3 | 38.1 | 101.7 |

Determination of a mechanism for the isolation of pyridostigmine by Sep-Pak cartridge Since the contents of Sep-Pak cartrides become basic when pyridostigmine bromide at pH 10 is added, the resulting retention of pyridostigmine can be postulated to be due to binding to negatively charged siloxy groups present on the silica, or binding as an ion-pair to the octadecylsilane phase attached to the silica. To resolve this, it is necessary to compare silica to which octadecyl groups were bound to a silica, preferably with the same number of binding sites, and also which did not have octadecyl groups bound to it. Corasil II met this requirement. Corsail II has approximately the same number of free siloxy groups as the octadecyl-bound silica used in the Sep-Pak.

Glass cartridges, patterned to approximately the same size and shape as the Sep-Pak cartridges, were filled with Corasil II and also $C_{18}$silica from the Sep-Pak. Experiments were run with 45 μg pyridostigmine bromide in 0.05M aqueous carbonate buffer (PH 10.5). Results shown in Table III indicate that pyridostigmine is strongly retained on silica which is not coated with organic phase.

Application of the method to biologial specimens

The assay was applied to the quantitation of pyridostigmine in urine and plasma of rats following the oral administration of 450 μg of pyridostigmine bromide per kg of body weight. One ml of urine and 1.5 ml of plasma samples were used for an assay. The urinary excretion of pyridostigmine in three rats over a 24-hour period was 60.0 and 65.4% of

TABLE III

RECOVERIES OF PYRIDOSTIGMINE BROMIDE FROM GLASS CARTRIDGES CONTAINING CORASIL II AND SEP-PAK $C_{18}$-SILICA

|  | Corasil II (pH 10.5) | Sep-Pak (pH 10.5) | Corasil II (aqueous) |
|---|---|---|---|
| Amount pyridostigmine bromide added (μg) | 45 | 45 | 45 |
| Sample eluate (5 ml) | 0 | 0.2 | 0 |
| Water wash (5 ml) | 0.5 | 0.9 | 0 |
| Methanol wash (5 ml) | 0 | 0.4 | 0 |
| Acetate-methanol (1 ml) | 6.8 | 31.8 | 0 |

TABLE III-continued

RECOVERIES OF PYRIDOSTIGMINE BROMIDE
FROM GLASS CARTRIDGES CONTAINING
CORASIL II AND SEP-PAK $C_{18}$-SILICA

|  | Corasil II (pH 10.5) | Sep-Pak (pH 10.5) | Corasil II (aqueous) |
|---|---|---|---|
| Acetate-methanol (1 ml) | 4.1 | 12.7 | 0.4 |
| Acetate-methanol (1 ml) | 2.6 | 1.7 | 0.6 |
| % Recovery | 30 | 103 | 2 | the total dose injected. Less than 5% was excreted between 24 and 48 hours. Initial plasma concentrations, using an average of three experiments for a single time point, were about 1/25 that of urine. Following a dose of approximately 80 μg per rat, average plasma levels of 250 ng/ml were determined after 7 min. Concentrations declined rapidly to less than 50 ng/ml within 1 hour.

Isolation of other types of aprotic compounds

In separate experiments, 2-ml aqueous solutions containing 25 μg/ml of acetylcholine, neostigmine, and edrophonium were adjusted to pH 10 and added to a Sep-Pak. Quantitative recoveries of these quaternary nitrogen compounds were obtained after elution with 2 ml of acetic acid in methanol.

Applicants have invented a novel method for the isolation and LC determination of polar compounds such as pyridostigmine and metabolites in aqueous fluids such as human urine and plasma. The drugs are separated at pH 10 with the aid of a Sep-Pak cartridge. The cartridge consists of a small plastic cylinder (6×7 mm) containing octadecylsilane bonded to porous 50-μm silica. Recoveries of pyridostigmine and metabolites added to human and rat urine and plasma are quantitative. Samples of urine or plasma (10 ml) can be extracted in less than 5 min with small volumes of solvents within a small laboratory space. Interferences from endogenous peaks from plasma were negligible and of minor nature from urine samples. In the ensuing analyses by LC a detection limit of 40 ng was obtained.

The method was applied to the determination of urinary excretion and plasma levels of pyridostigmine in rats following intramuscular administration. Levels were consistent with those reported by Birtley et al. in Brit. J. Pharmacol. Vol. 26, (1966), page 393, in which radio-labeled drug was used.

The instant method of this invention was also used to isolate aqueous solutions of aliphatic and aromatic quarternary nitrogen compounds such as acetylcholine, neostigmine and edrophonium.

Possible mechanisms involved in the isolation of pyridostigmine in the reversed-phase cartridge are discussed below. In classical paired-ion reversed-phase chromatography the retention of an ionic species is enhanced by the addition of an organic counter-ion in the mobile phase. Applicants have found that polar inorganic counter-ions such as hydroxide, carbonate, and phosphate caused quantitative binding of pyridostigmine but not its metabolites on the Sep-Pak reversed-phase column. Chloride and bromide ions caused lower affinities for binding. Either ion-pair formation, binding to siloxy groups present in the Sep-Pak, or possibly both effects could account for the binding of pyridostigmine. Organic solvents of various polarities could not extract pyridostigmine from basic solutions. Corasil II, containing a similar number of free binding sites as the Sep-Pak strongly retained pyridostigmine. Here, pyridostigmine could not be eluted with acetate—methanol. Thus, it is likely that the isolation mechanism involves both ion-pair formation with hydroxide and the binding of the quaternary compound to siloxy groups. It is not clear why pyridostigmine in aqueous solutions, but not in urine, at pH values 8–9.5, can be recovered quantitatively. A possible explanation is that siloxy sites are not as available as pH decreases, and that compounds in urine may compete for these sites. Resulting ion-pair affinities of these inorganic counter-ions used in the isolation of pyridostigmine by the Sep-Pak are in reverse order to those reported for similar counter-ions in the basic efforts of Modin and Schill in *Acta. Pharm. Suecica*, Vol. 4, (1967), page 301 and Borg in *Acta. Pharm. Suecica*, Vol. 8, (1971), page 11.

A practical biological consideration of this work could apply to the way polar organic molecules are able to pass into lipid membranes. Results in this paper provide a mechanism as to how polar compounds can cross such barriers. Aprotic polar compounds could form an ion-pair with inorganic ions present in the body and be absorbed by a lipid membrane in a manner similar to that by which they are bound to the reversed-phase silicone system. The amount that is bound would depend both on the structure of the compound as well as the concentration of the inorganic counter-ion. Perhaps only small amounts of a drug would cross lipid barriers, but then only a small amount of drug entering a cell may be all that is required to sustain a therapeutic effect.

We claim:

1. A method for separating a polar compound selected from the group consisting of pyridostigmine, acetylcholine, neostigmine, and edrophonium and metabolites thereof from an aqueous solution comprising the steps of:
   a. washing a cartridge which is packed with a packing material of silanized silica gel coated with octadecyl silane with an alkanol containing 1 to 7 carbon atoms, then washing said cartridge with water;
   b. preparing an alkaline solution of said aqueous solution by adding a sufficient amount of base to said aqueous solution to adjust its pH level to within the range of 10 to 11;
   c. recovering the alkaline solution prepared in step b.;
   d. passing the alkaline solution recovered in step c. through said alkanol and water washed cartridge of step a. to cause said compound and metabolites thereof to bind to said packing material within the cartridge; and
   e. separating the compound and metabolites thereof bound to the packing material within the cartridge of step d. by washing the cartridge with successive washings of water, an alkanol, and alkanol dilute acid-alkanol mixtures wherein the alkanol component contains 1 to 7 carbon atoms and collecting resultant liquid fractions containing said compound and metabolites.

2. The method of claim 1 wherein said polar compound is acetylcholine.

3. The method of claim 1 wherein said polar compound is neostigmine.

4. The method of claim 1 wherein said polar compound is pyridostigmine.

5. The method of claim 1 wherein the alkanol in each of steps a. and e. is methanol.

6. The method of claim 1 wherein the pH level is within the range of 10.02 to 10.6.

7. The method of claim 6 wherein the pH level is within the range of 10.2 to 10.6.

8. The method of claim 1 wherein the acid in the alkanol dilute acid-alkanol mixtures is selected from the group consisting of acetic acid and hydrochloric acid.

9. The method of claim 8 wherein the acid in the alkanol dilute acid-alkanol mixtures is acetic acid.

10. The method of claim 1 wherein the base is selected from the group consisting of alkali metal hydroxides and alkali metal carbonates.

11. The method of claim 10 wherein the base is sodium hydroxide.

12. The method of claim 10 wherein the base is sodium carbonate.

13. The method of claim 1 wherein the aqueous solution is selected from the group consisting of water, urine and plasma.

14. The method of claim 13 wherein the aqueous solution is water.

15. The method of claim 13 wherein the aqueous solution is urine.

16. The method of claim 13 wherein the aqueous solution is plasma.

17. The method of claim 1 wherein the aqueous solution is selected from the group consisting of water, urine and plasma; the base is sodium hydroxide; the pH level is within the range of 10.2 and 10.6; the acid in the alkanol dilute acid-alkanol mixtures is 0.1N acetic acid; and the alkanol in steps a. and e. is methanol.

18. The method of claim 17 wherein the cartridge is Sep-Pak ™.

19. The method of claim 18 wherein said polar compound is pyridostigmine.

20. A method for measuring the amount of pyridostigmine and its metabolites in a plasma sample comprising the steps of:
   a. washing a cartridge which is packed with a packing material of silanized silica gel coated with octadecyl silane with an alkanol containing 1 to 7 carbon atoms, then washing said cartridge with water;
   b. preparing an alkaline solution of the plasma sample by adding sufficient base to the plasma sample to adjust its pH level to within the range of 10 to 11;
   c. recovering the alkaline solution prepared in step b.;
   d. passing the alkaline solution recovered in step c. through said alkanol and water washed cartridge of step a., to cause the pyridostigmine and its metabolites to bind to said packing material within the cartridge;
   e. separating the pyrdostigmine and its metabolites bound to the packing material within the cartridge of step d. by washing the cartridge with successive washings of water, an alkanol, and alkanol dilute acid-alkanol mixtures wherein the alkanol component contains 1 to 7 carbon atoms and collecting resultant liquid fractions containing pyridostigmine and its metabolites;
   f. drying each fraction of step e. over nitrogen;
   g. adding a methanol solution to each dried fraction of step f.; and
   h. injecting a volume of each methanolic fraction prepared in step g. equivalent to 1 ml of plasma into a liquid chromatograph for quantitative analysis.

21. A method for measuring the amount of pyridostigmine and its metabolites in a urine sample comprising the steps of:
   a. washing a cartridge which is packed with a packing material of silanized silica gel coated with octadecyl silane with an alkanol containing 1 to 7 carbon atoms, then washing said cartridge with water;
   b. preparing an alkaline solution of the urine sample by adding sufficient base to the urine sample to adjust its pH level to within the range of 10 to 11;
   c. recovering the alkaline solution prepared in step b.
   d. filtering the alkaline solution recovered in step c.;
   e. passing the filtered alkaline solution of step d. through said alkanol and water washed cartridge of step a., to cause the pyridostigmine and its metabolites to bind to said packing material within the cartridge;
   f. separating pyridostigmine and its metabolites bound to the packing material within the cartridge of step e. by washing the cartridge with a dilute acid-alkanol mixture successive washings of water, an alkanol, and alkanol dilute acid-alkanol mixtures wherein the alkanol component contains 1 to 7 carbon atoms and collecting resultant liquid fractions containing pyridostigmine and its metabolites;
   g. drying each fraction of step f. over nitrogen;
   h. adding methanol solution to each dried fraction of step g.; and
   i. injecting a volume of each methanolic fraction prepared in step h. equivalent to 1 ml of urine into a liquid chromatograph for quantitative analysis.

* * * * *